United States Patent [19]
Spitz

[11] Patent Number: 5,256,133
[45] Date of Patent: Oct. 26, 1993

[54] DEVICE FOR CORRECTING STRESS URINARY INCONTINENCE

[76] Inventor: Robert M. Spitz, 58 Gallup La., Waterford, Conn. 06385

[21] Appl. No.: 648,654

[22] Filed: Jan. 31, 1991

Related U.S. Application Data

[63] Continuation-in-part of Ser. No. 578,124, Sep. 5, 1990, abandoned.

[51] Int. Cl.⁵ .................................................. A61F 2/00
[52] U.S. Cl. .............................. 600/29; 600/30; 128/DIG. 25
[58] Field of Search ................................ 600/29, 30; 128/DIG. 25; 606/139, 184, 188, 228, 232

[56] References Cited
U.S. PATENT DOCUMENTS

| | | | |
|---|---|---|---|
| 4,592,356 | 6/1986 | Gutierrez | 606/232 |
| 4,780,492 | 6/1988 | Jacobs | 606/332 |
| 4,873,976 | 10/1985 | Schreiber | 606/332 |
| 4,969,892 | 11/1990 | Burton et al. | 606/232 |
| 4,976,715 | 12/1990 | Bays et al. | 606/232 |
| 5,013,292 | 8/1991 | Lemay | 128/DIG. 25 |

*Primary Examiner*—Randall L. Green
*Assistant Examiner*—K. Reichle
*Attorney, Agent, or Firm*—McCormick, Paulding & Huber

[57] ABSTRACT

Female stress urinary incontinence is corrected by implanting a correcting device which supports the urethrovesical junction from the abdominal fascia. A trocar/cannula assembly is inserted upwardly through the vaginal wall immediately adjacent or proximate the urethrovesical junction, through the space of Retzius, and through the abdominal fascia. The trocar is then removed from the cannula after which the correcting device is loaded into the cannula and pushed upwardly through it and to an implanted position using a push rod. Thereafter the push rod and cannula are removed to complete the procedure.

38 Claims, 7 Drawing Sheets

DEVICE FOR CORRECTING STRESS URINARY INCONTINENCE

This is a continuation-in-part of application Ser. No. 578,124, filed Sep. 5, 1990, now abandoned.

BACKGROUND OF THE INVENTION

This invention relates to improvements in devices and method for correcting female stress urinary incontinence.

Currently accepted methods for surgically correcting anatomic defects leading to stress urinary incontinence involve various suturing techniques for elevating the urethrovesical junction (UVJ). Such surgical procedures generally include abdominal incision and require that the patient be hospitalized.

It is the general aim of the present invention to provide an improved device for correcting female stress urinary incontinence which includes a correcting element for elevating the UVJ and an improved method for implanting a correcting element through the vagina to elevate the UVJ without abdominal incision. It is a further aim of the invention to provide a method for correcting stress urinary incontinence which may be performed as an outpatient procedure to eliminate the need for hospitalization.

SUMMARY OF THE INVENTION

In accordance with the present invention an improved device for correcting female stress urinary incontinence comprises implant means for supporting an associated portion of the vaginal wall in elevated position relative to the abdominal fascia. The implant means includes an axially elongate connecting member and retaining means for securing one end portion of the connecting member proximate the abdominal fascia to support the implant means and including at least one resilient flexible retaining member having a deployed position wherein it projects laterally outwardly from the connecting member and an inserting position wherein it is disposed laterally inwardly of its deployed position in the direction of said connecting member. The retaining member is resiliently self-biased toward its deployed position. A supporting means which comprises a part of the implant means is attached to said connecting means in axially spaced relation to said retaining means for supporting the associated portion of the vaginal wall in elevated position. The implant means is implanted through the vagina with the retaining member held in its inserting position. The retaining member is released from its inserting position when the implant means attains its implanted position.

DETAILED DESCRIPTION OF PREFERRED EMBODIMENTS AND METHODS

Figures 1, 5:
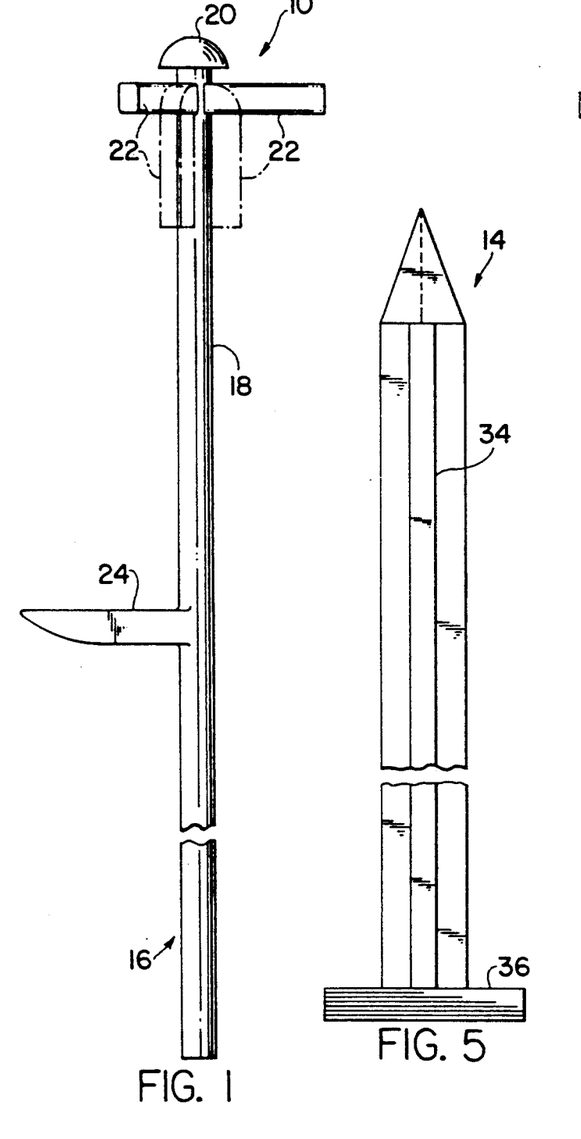
FIG. 1 is a side elevational view of a correcting element which comprises a part of a device for correcting stress urinary incontinence and embodying the present invention.
FIG. 5 is a fragmentary side elevational view of a trocar which comprises another part of the device.
Figure 2:
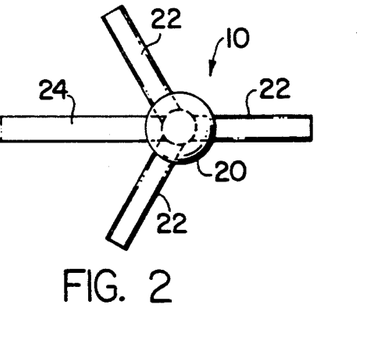
FIG. 2 is a plan view of the correcting element shown in FIG. 1.
Figure 3:
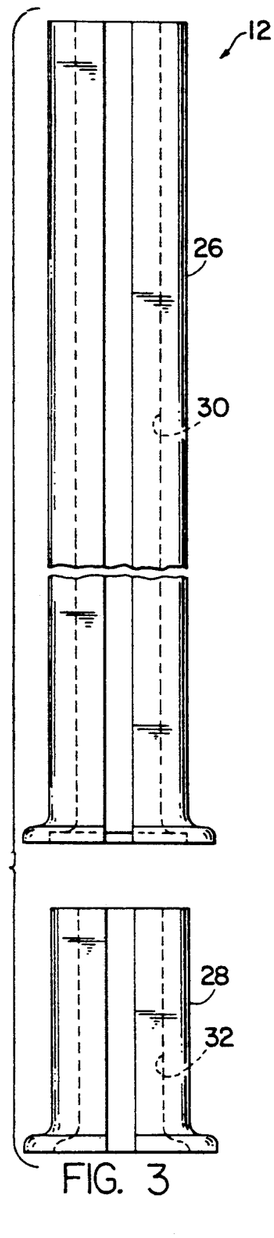
FIG. 3 is an exploded fragmentary side elevational view of a cannula assembly which comprises part of the device and which is used for implanting the correcting element.
Figure 6:
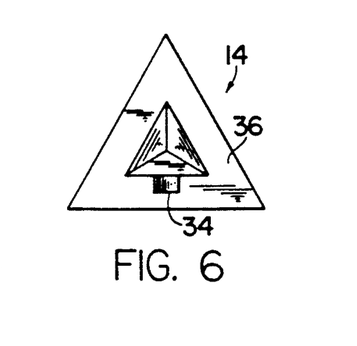
FIG. 6 is a top plan view of the trocar.

Turning now to the drawings, a device for correcting stress urinary incontinence and embodying the present invention comprises a correcting element indicated generally by the reference numeral 10, best shown in FIGS. 1 and 2, and other elements which comprise an instrument used for implanting the correcting element 10 in a patient. More specifically, in addition to the correcting element 10 the device further includes a cannula assembly, designated generally by the numeral 1, and which comprises a cannula body 26 and a cannula extension 28 best shown in FIGS. 3 and 4, a trocar illustrated in FIGS. 5 and 6 and indicated generally at 14, and a push rod designated generally by the numeral 16, which comprises an integral part of the correcting element 10 shown in FIGS. 1 and 2. In the detailed description of the device which follows and in the claims, relative terms, such as upper and lower, are employed, for convenience, and refer to the device as oriented in the drawings.

Referring now particularly to FIGS. 1 and 2 the correcting element 10 preferably comprises a unitary structure molded from a somewhat flexible resilient biocompatible alloplastic material such as a polymer, for example. It includes an elongate connecting member or stem portion 18 which has an enlarged head 20 at its upper end. At least one retaining member 22 is connected in cantilever position to the stem 18 immediately below the head 20. However, the presently preferred correcting element 10 has three such retaining members or cross arms 22, which are preferably equangularly spaced about the axis of the stem 18 and which lie generally within a common axial plane relative to the stem. Each retaining member 22 has a deployed or retaining position, shown in full line in FIG. 1, wherein it extends generally laterally outwardly from the stem. Each retaining member 22 is resiliently self-biased toward its deployed position and deflectable downwardly from its deployed position of FIG. 1 to an inserting position, indicated by broken lines, wherein it is disposed generally adjacent the stem 18. More specifically, the retaining members 22 are preferably arranged for hinged flexure in one direction or downwardly relative to the stem 18. The enlarged head 20 prevents or at least limits deflection of the retaining members 22 in an upward direction beyond the deployed position.

A supporting member 24 integrally connected in cantilever position to the stem 18 in downwardly spaced relation to the retaining members 22 projects generally laterally outwardly from the stem. The portion of the stem 18 below the support member 24 defines the integral push rod 16 used to move and position the correcting element 10 during the implanting procedure, as will be hereinafter further discussed.

Figure 4:
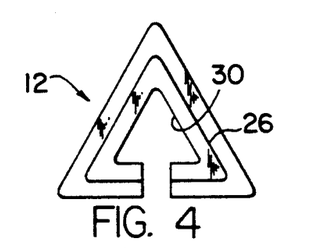
FIG. 4 is a top plan view of the cannula.

The elongate cannula body 26 is used in conjunction with the trocar 14 during the implanting procedure. The separable cannula extension 28 is adapted for mating engagement with the cannula body 26 within a shallow recess in the lower end of the cannula body to form a coaxial extension of the body. A laterally outwardly open main channel 30 is defined by and extends throughout the length of the cannula body 26 and has a generally triangular cross section, substantially as shown in FIG. 4. The cannula extension 28 defines a secondary channel 32 which forms a substantially longitudinal extension of the main channel 30 when the cannula extension is assembled in mating engagement with the cannula body 26, as will be hereinafter more fully discussed.

When the sharp-pointed trocar 14 is received within the main channel 30 defined by the cannula body a rib 34, which projects from and extends generally along the length of the trocar, is received within and substantially fills the channel opening in the wall of the cannula body. Thus, the cross section of the trocar substantially complements the cross section of the main channel 30, so that the trocar/cannula assembly (FIG. 7) presents a substantially uninterrupted triangular peripheral surface throughout its length. When the trocar 14 is assembled with the cannula body 26, the sharp-pointed upper end of the trocar 14 is exposed above the upper end of the cannula body. A flange 36 at the lower end of the trocar engages the lower end of the cannula body 26 to limit upward movement of the trocar within and relative to the cannula body, as shown in FIG. 7.

Figure 7:
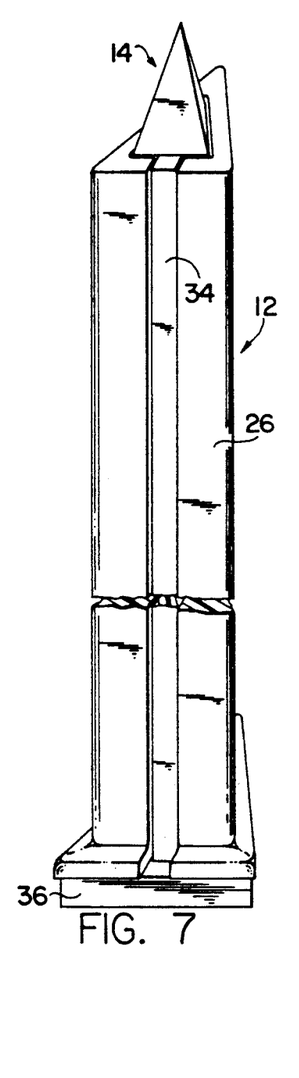
FIG. 7 is a fragmentary perspective view of the trocar/cannula assembly.

Preparatory to implanting the correcting element 10, the trocar 14 is assembled with the cannula body 26, as shown in FIG. 7. Thereafter the trocar/cannula assembly is pushed upwardly through the vaginal wall, piercing the wall immediately adjacent or proximate the urethrovesical junction, through the Space of Retaus, and through the abdominal fascia. This procedure is preferably performed while viewing the inside of the bladder through a cystoscope to ensure that the bladder is not injured. The trocar 14 is then removed from the cannula body 26 leaving the upper end of the cannula body 26 in a position above the abdominal fascia.

Figure 8:
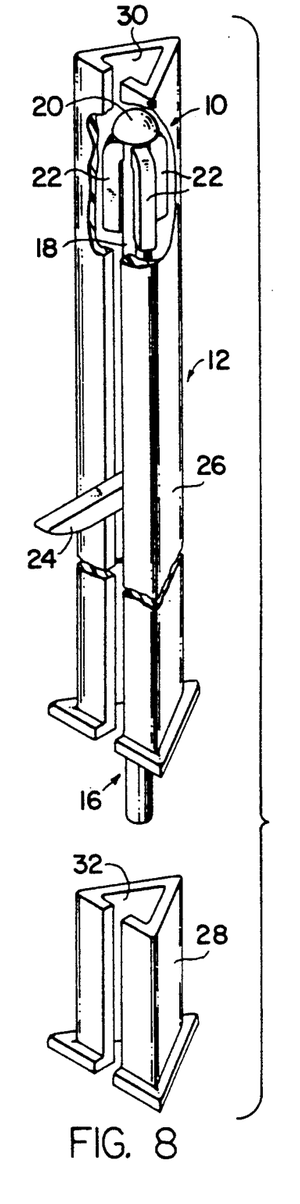
FIG. 8 is an exploded fragmentary perspective view of the cannula body and cannula extension and shows the correcting device positioned within the cannula body.

The correcting element 10 is next loaded into the cannula extension 28 with the cross arms 22 thereof deflected or folded downward to inserting position adjacent the stem 18. Using the push rod 16 to manipulate the cannula extension 28 it is brought into mating engagement with the lower end of the cannula body 26 so that the secondary channel 32 containing the upper end portion of the correcting member 10 is generally coaxially aligned with the main channel 30. Thereafter, utilizing push rod 16 the correcting element 10 is moved upwardly from the secondary channel into the main channel 30 with the supporting member 24 extending outwardly from the channel as shown in FIG. 8. When the correcting element 10 is disposed within the main channel 30 the cannula extension 28 may be removed.

Figure 9:
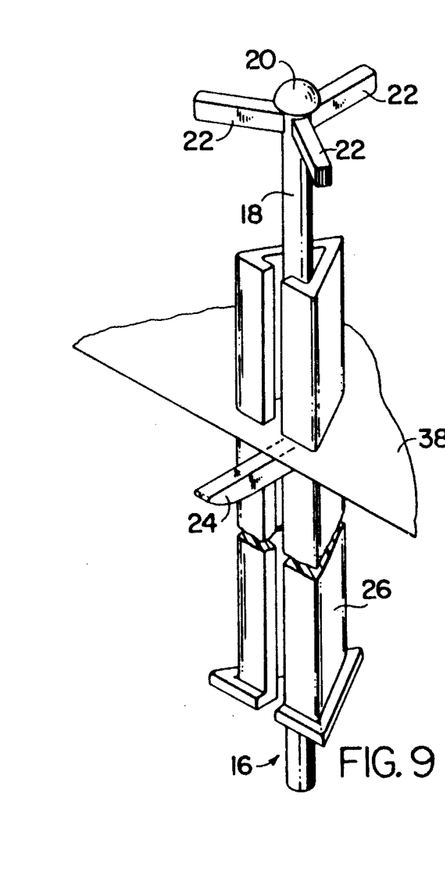
FIG. 9 is a somewhat schematic fragmentary perspective view and shows the cannula body and correcting element at one stage of the implanting procedure.
Figure 10:
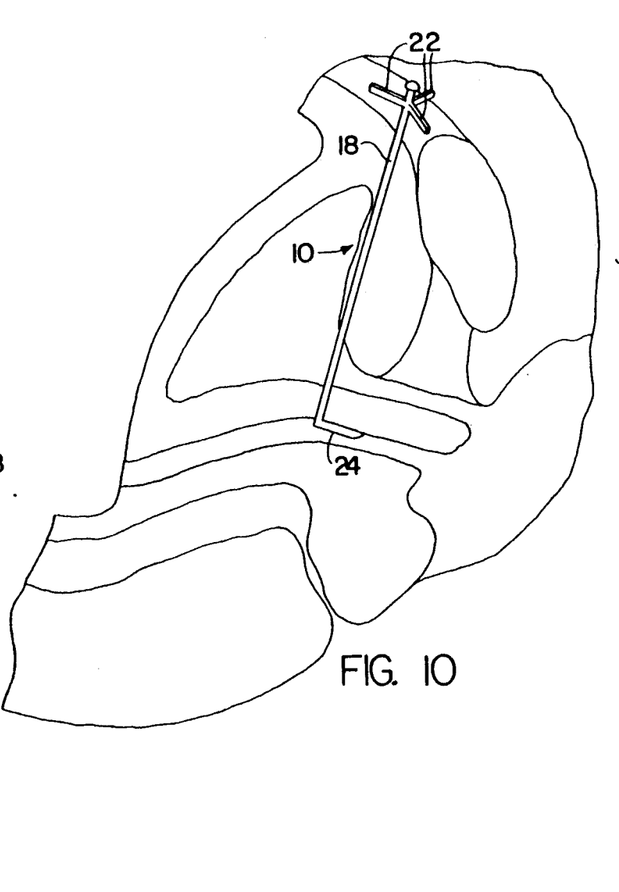
FIG. 10 is a somewhat schematic female abdominal section shown with a correcting element in implanted position.

The correcting element 10 is moved upwardly through and beyond the upper end of the main channel 30 to a position wherein the retaining members 22 are disposed a sufficient distance above the abdominal fascia to allow the then unrestrained resiliently-biased retaining members 22 to return to deployed or retaining position above the abdominal fascia. The latter position of the correcting member is illustrated somewhat schematically in FIG. 9 where the abdominal fascia is indicated by the numeral 38. When the correcting element 10 has attained its implanted position, wherein the retaining members are disposed above the abdominal fascia and the supporting member is disposed in supporting and elevating relation to the urethrovesical junction, the cannula body 26 is withdrawn from assembly with the correcting element 10 leaving the latter element in its implanted position of FIG. 10. The procedure is completed by severing the push rod 16 from the stem 18 immediately below the supporting member 24.

Figure 11:
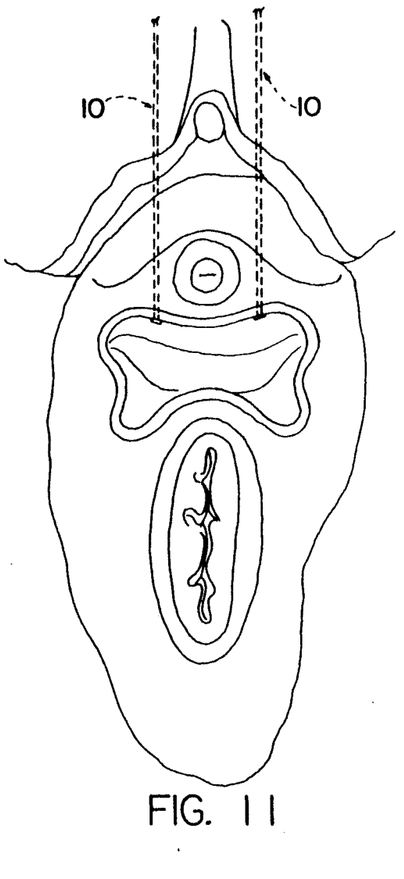
FIG. 11 is a somewhat schematic fragmentary front abdominal view of a female and shows two correcting elements in implanted position.

The implantation procedure has been described with reference to a single correcting element 10. However, in accordance with the presently preferred procedure, two such correcting elements are implanted to support the urethrovesical junction, one of the correcting elements being disposed to each side of the urethra in spaced apart relation to each other, as shown in FIG. 11. Since the aforedescribed implanting method does not require abdominal incision, under ordinary circumstances the procedure may be performed as an outpatient procedure without necessity for hospitalization.

In FIGS. 12-17 the various elements which comprise another device for correcting stress urinary incontinence and embodying the present invention are shown. The illustrated device includes a correcting element, indicated generally at 10a, a cannula designated generally by the numeral 12a, a trocar shown generally at 14a and a push rod indicated generally at 16a.

Figures 12, 13, 14, 15, 16, 17:
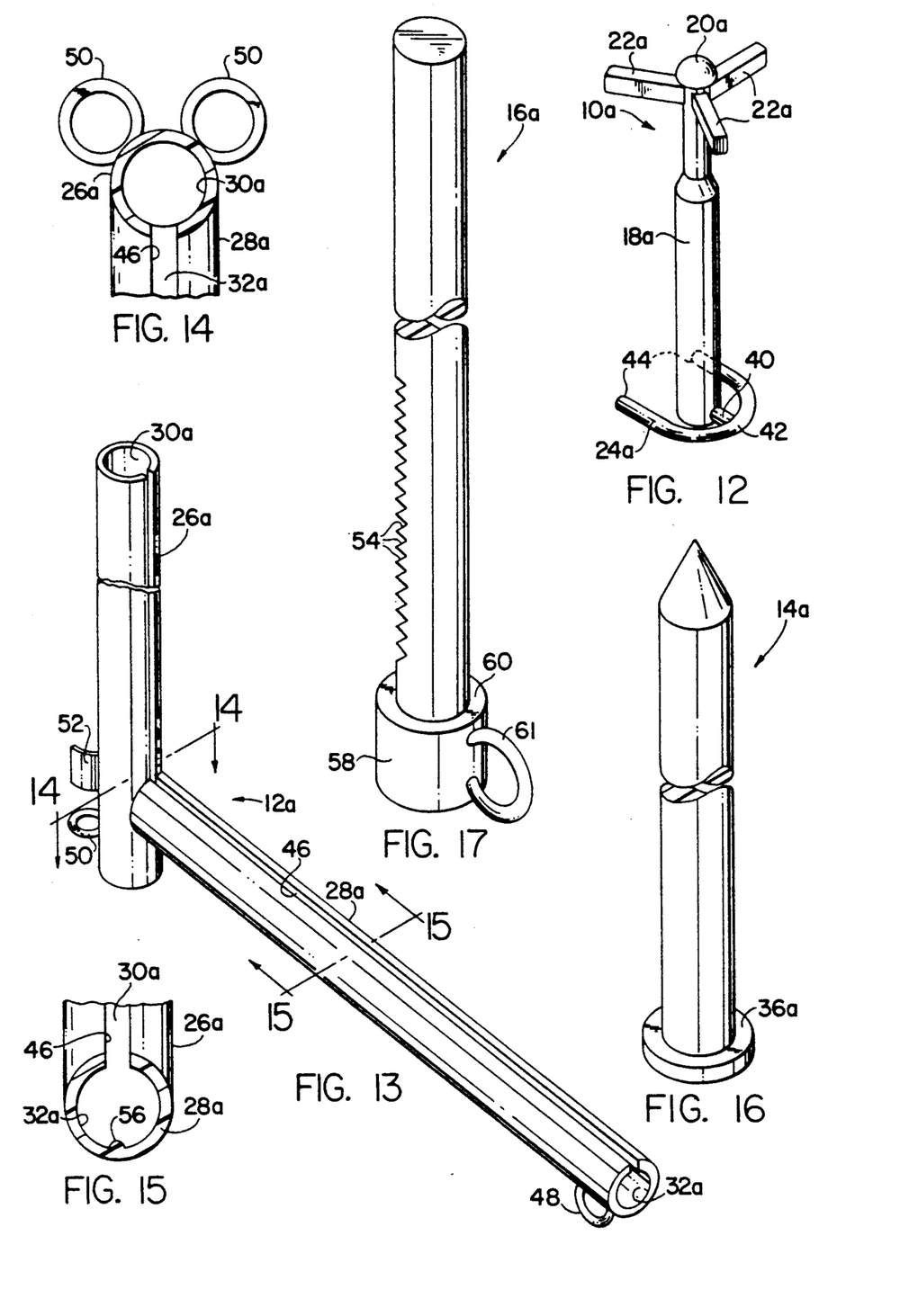
FIG. 12 is a perspective view of another correcting element embodying the present invention.
FIG. 13 is a fragmentary perspective view of another cannula used for implanting the correcting element shown in FIG. 12.
FIG. 14 is a fragmentary sectional view taken along the line 14—14 of FIG. 13.
FIG. 15 is a fragmentary sectional view taken along the line 15—15 of FIG. 13.
FIG. 16 is a trocar for use with the cannula of FIG. 13.
FIG. 17 is a perspective view of a push rod for use with the cannula of FIG. 13.

The correcting element 10a is similar in many respects to the correcting element 10, previously described, but differs therefrom in the construction and arrangement of its supporting member 24a. Specifically, the supporting member 24a has a connecting portion 40 attached in cantilever position to the lower end portion of the stem 18a and projecting laterally outwardly from the stem. A generally U-shaped reverse bend portion 42 is connected to the outer or free end of the connecting portion 40 and carries a pair of generally parallel spaced apart legs 44, 44 which are disposed in a radial plane relative to the stem and extend in the general direction of the stem. The supporting member 24a provides support for a somewhat larger area of vaginal wall than can be supported by the corresponding supporting member 24 of the previously described correcting element 10.

The cannula 12a, shown in FIG. 13 has an elongate generally tubular body 26 a including a cylindrical bore which extends throughout its length. A cannula extension, indicated at 28a, comprises an integral branch of the cannula body and projects from the lower end portion of the cannula body. An outwardly open slot 46 extends along the length of the cannula extension 28a and the portion of the cannula body 26a above the extension and communicate 5 with the bores of both the cannula body and cannula extension to define a main channel 30a within the upper portion of the cannula body and a secondary channel 32a within the cannula extension which communicates with the main channel 30a. Appendages on the cannula provide a means for manually manipulating and guiding the cannula during the implantation procedure. The construction and arrangement of these guide appendages may vary, but in accordance with the presently preferred construction a single finger ring 48 located at the lower end of the cannula extension is provided for this purpose. A pair of additional finger rings 50 and a finger plate 52 are carried by the cannula body 26a to further facilitate manual manipulation.

The trocar 14a may take various forms, but preferably, and as shown, it comprises a cylindrical member adapted to be slidably received within the cannula body 26a and has a sharp-pointed upper end and a diametrically enlarged flange 36a at its lower end.

As previously noted, the push rod 16a comprises a separate member made from flexible material and adapted to be slidably received within the secondary bore 32a. A longitudinal series of detent notches 54 formed in the push rod, substantially as shown, cooperate with a detent projection 56 on the wall of the cannula extension 28a which projects into the secondary channel 32a, for a purpose which will be hereinafter further evident. A diametrically enlarged lower end portion of the push rod, indicated at 58, defines an annular abutment 60 which cooperates with the lower end of the cannula extension to form a limit stop for arresting movement of the push rod 16 a into the cannula extension 28a. A thumb ring 61 at the lower end of the push rod 16a aids in manual manipulation of the rod.

Preparatory to implanting the device, the trocar 14a is loaded into the main channel 30a and the correcting element 10a is loaded into the secondary channel 32a. The push rod 16a is also inserted into the secondary channel below the correcting element and to a position wherein the first detent notch on the push rod is engaged with the detent projection on the cannula extension to hold the push rod in place while the device is being inserted into the patient.

The trocar/cannula assembly is pushed upwardly through the vaginal wall piercing the wall immediately adjacent or proximate the urethrovesical junction, through the space of Retaus, and through the abdominal fascia, in the manner generally aforedescribed, while the inside of the bladder is preferably viewed through a cystoscope. When the upper end of the cannula body 26a reaches a position above the abdominal fascia the trocar 14a is removed.

The flexible push rod is now used to push the correcting member 10 a upwardly through the secondary channel 32a and into and upwardly through the main channel 30a. The detent notches on the push rod cooperate with the detent projection in the secondary channel to aid in controlling the push rod. A count of the detent notches passed as the push rod advances may also serve to indicate the position of the correcting member relative to the cannula as the procedure progresses.

The upper end of the correcting member 10a is moved through and beyond the upper end of the main channel 30a to a position wherein the self-biased cross arms 22a, 22a are no longer restrained and are free to return to deployed or retaining position above the abdominal fascia. The cannula 12a with the push rod therein may then be withdrawn from the patient to complete the procedure.

Figure 18:
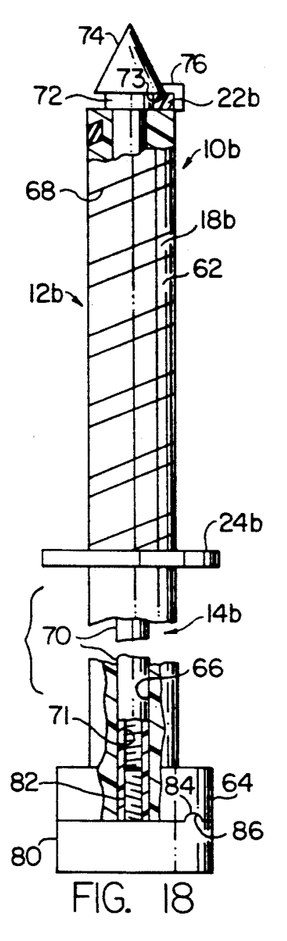
FIG. 18 is a fragmentary side elevational view of another device for correcting stress urinary incontinence and embodying the invention.
Figure 19:
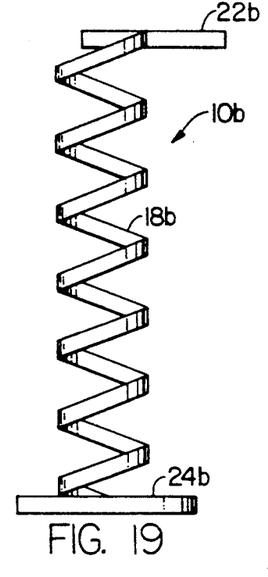
FIG. 19 is a side elevational view of a correcting element which comprises a part of the device shown in FIG. 18.

Referring now to FIG. 18 a further device for correcting stress urinary incontinence and embodying the invention is shown in assembly ready for use. The various components which comprises the device include an implant or correcting element and a cannula and trocar generally indicated at 10b, 12b and 14b, respectively, which comprise an instrument for implanting the correcting element 10b. Details of these individual components are shown in FIGS. 19-23.

Figure 20:
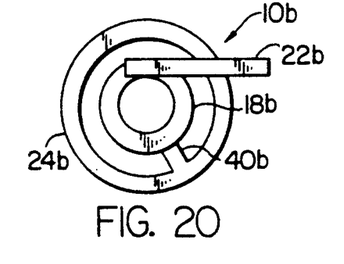
FIG. 20 is a top plan view of the correcting element of FIG. 18.

The illustrated correcting element 10b is preferably made from a resilient flexible alloplastic material and includes an axially elongate stem which comprises a helix or helicoid 18b having a uniform diameter throughout its length. The helix 18b is right-handed and advances downwardly onto the cannula 12b when rotated in clockwise direction relative to the cannula, as viewed from above in FIG. 20. An integral retaining member 22b connected in cantilever position to the upper end of the helix 18b extends tangentially outwardly from it in clockwise direction as viewed from above (FIG. 20) and to a deployed or retaining position in which it appears in FIGS. 19 and 20. The retaining member 22b is resiliently self-biased to its deployed position and is deflectable to an inserting or implanting position wherein it at least partially encircles the axis of the helix 18b, as will be hereinafter further discussed. A generally circular support member 24b is connected in coaxial relation to the lower end of the helix 18b by an integral connecting member 40b, substantially as shown in FIG. 20.

Figure 21:
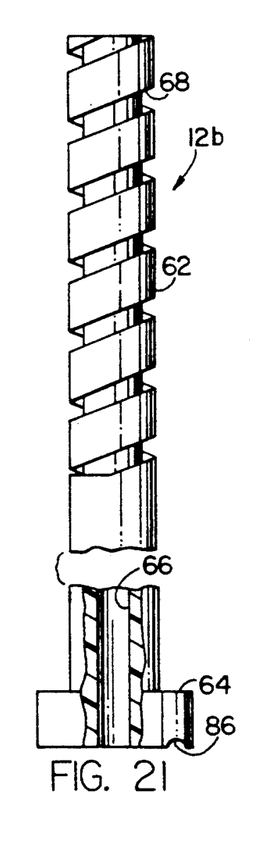
FIG. 21 is a side elevational view of a cannula which comprises a part of the correcting device shown in FIGS. 18 and 19.
Figure 22:
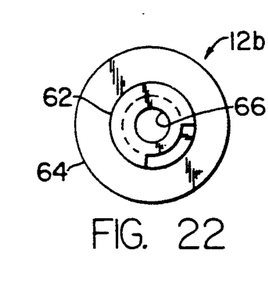
FIG. 22 is a top plan view of the cannula shown in FIG. 21.

The cannula 12b used to implant the correcting member 10b is shown in FIGS. 21 and 22 and has an axially elongate generally cylindrical body portion 62 and a diametrically enlarged generally cylindrical flange 64 at its lower end. A generally cylindrical bore 66 extends coaxially through the cannula 12b as shown in FIG. 21. The correcting element 10b is adapted to be threaded onto the cannula 12b and for this reason a helical groove 68 is formed in the upper part of the body portion 62 to complement the helix 18b.

Figure 23:
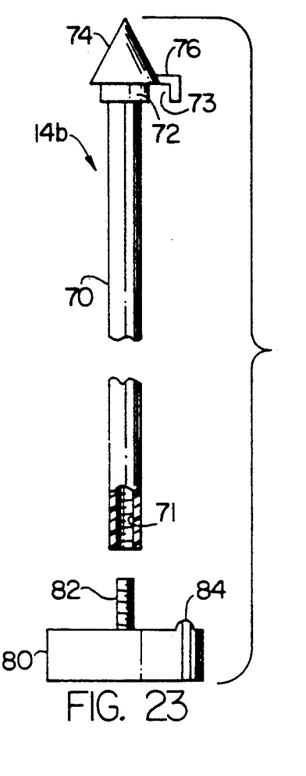
FIG. 23 is an exploded side elevational view of a trocar for use with the cannula shown in FIGS. 21 and 22.

Referring now to FIG. 23, the illustrated trocar 14b is adapted to the slidably received within the bore 66 and supported therein for coaxial rotation relative to the cannula. The trocar includes an axially elongate shank 70 having a threaded opening 71 in its lower end and a length substantially equal to the length of the cannula 12b. At its upper end the shank 70 has a diametrically enlarged generally cylindrical portion 72. The trocar further includes a conical upper end portion 74 which diverges upwardly from the cylindrical portion 72. A winding key 76 projects radially outwardly from the base of the conical portion 74 and cooperates with the cylindrical portion 72 to define a downwardly open notch 73 which receives the retaining member 22b, for a purpose which will be hereinafter evident.

The trocar 14b further includes a generally cylindrical turn piece 80 which carries a threaded stud 82 adapted to be threadably received within the threaded opening 71. It should be noted that the thread on the stud 82 is of opposite hand from the convolutions of the helix 18b. A detent projection 84 on the upper surface of the turn piece 80 is adapted to cooperate in snap-in engagement within a detent recess 86 formed in the lower surface of the flange 64 when the trocar 14b is assembled with the cannula 12b, as will be hereinafter discussed.

Preparatory to implanting the device the correcting element 10b is threaded onto the upper end portion of the cannula 12b. The correcting element 10b is rotated in clockwise direction as viewed from above and relative to the cannula until it is fully seated thereon. In assembly the correcting element 10b cooperates with the cannula 12b to define a substantially uninterrupted generally cylindrical peripheral surface.

The trocar shank 70 is next inserted downwardly through the bore 66 until the cylindrical portion 72 is seated on the upper end of the cannula with the retaining member 22b disposed within the notch 73. The turn piece 80 is now attached to the lower end of the trocar by threading the stud 82 into the threaded opening 71 by rotating the turn piece 80 in a counterclockwise direction relative to the cannula as viewed from below. After the stud 82 has been fully threaded into the shank 70 further counterclockwise rotation of the turn piece 80 relative to the cannula will result in corresponding rotation of the trocar 14b causing the key 76 to wind the retaining member about the axis of the helix 18b and onto the cylindrical portion 72 and to an implanting position. The trocar and cannula are so constructed and arranged that the detent 84 engages the detent recess 86 when the retaining member 22b is wound to its proper inserting position in which position it is retained by the winding key 76.

In accordance with the preferred implantation procedure the assembly shown in FIG. 18 and hereinbefore described is pushed upwardly through the vaginal wall immediately adjacent or proximate the urethrovesical junction puncturing the latter wall. The device is passed upwardly through the space of Retaus and to a position proximate the abdominal fascia, that is above the abdominal fascia or within the tissue below the abdominal fascia. This procedure is preferably performed while the inside of the bladder is viewed through a cystoscope to assure that no bladder damage occurs.

The support member 24b is brought into engagement with an associated portion of the vaginal wall to elevate the wall while the retaining member is being positioned relative to the abdominal fascia. When the latter condition is attained the lower end portion 80 is further rotated in counterclockwise direction relative to the cannula as viewed from below which causes the winding key 76 to release the retaining member 22b from its implanting position whereupon the retaining member is resiliently self-biased to its deployed or retaining position proximate the abdominal fascia. The turn piece 80 is now rotated in counterclockwise direction relative to the correcting element 10b as viewed from below to separate the cannula 12b, trocar 14b and turn piece 80 as a unit from the correcting element 10b, which remains in its implanted position within the patient.

Each embodiment of the invention previously described includes a support member which is disposed below the vaginal wall and which serves to both elevate and support the wall. In the further embodiments of the invention hereinafter described elevation and support for the vaginal wall is achieved without positioning the support member below the vaginal wall and within the vagina.

Figures 24, 25, 27:
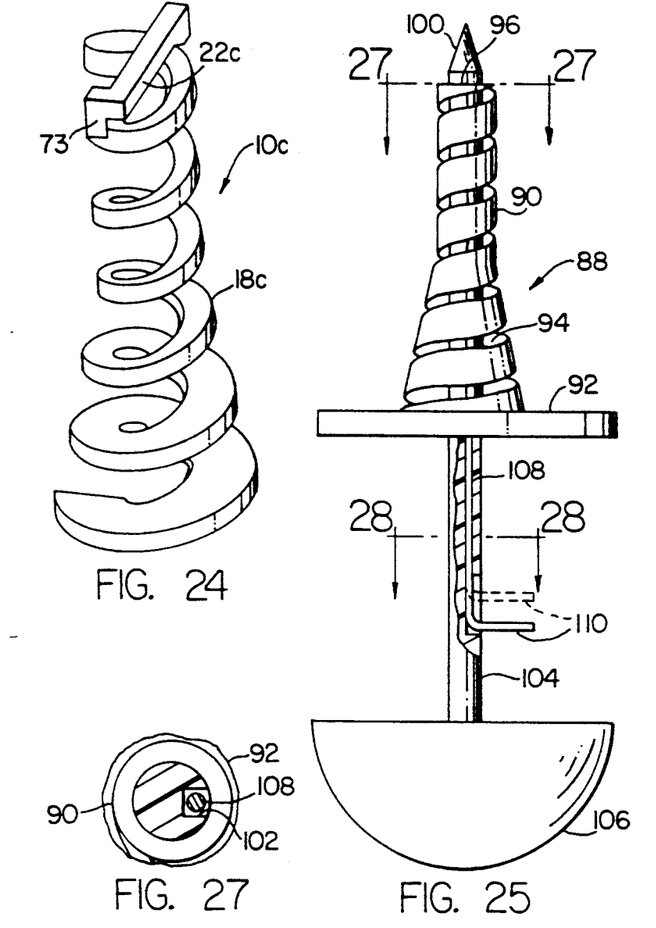
FIG. 24 is a perspective view of yet another correcting element.
FIG. 25 is a side elevational view of an instrument for use in implanting the correcting element shown in FIG. 24.
FIG. 27 is a somewhat enlarged fragmentary sectional view taken along the line 27—27 of FIG. 25.
Figure 26:
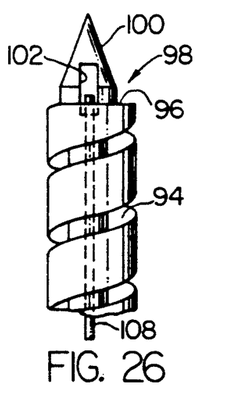
FIG. 26 is a somewhat enlarged fragmentary end elevational view of the instrument shown in FIG. 25.
Figure 28:
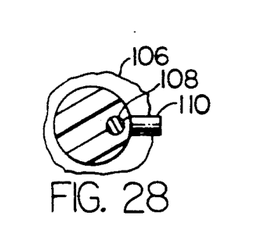
FIG. 28 is somewhat further enlarged fragmentary sectional view taken along the line 28—28 of FIG. 25.
Figure 29:
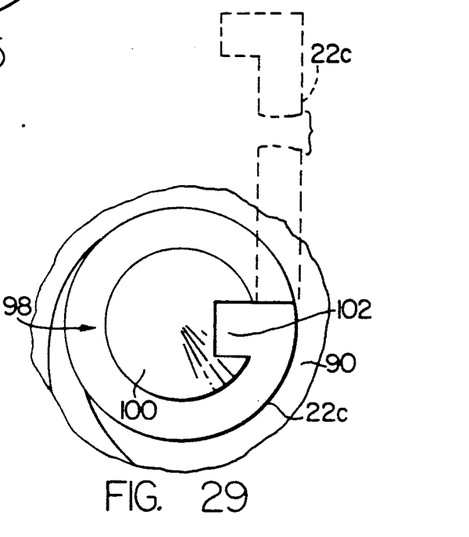
FIG. 29 is a somewhat enlarged fragmentary top plan view of the instrument of FIG. 25 shown with a correcting element in implanting position thereon.

Referring now to FIGS. 24-29 still another device embodying the invention is illustrated and described and includes a correcting element shown in FIG. 24 and indicated generally by the reference numeral 10c. The illustrated correcting element 10c is preferably made from a resilient flexible alloplastic material and has an axially elongate stem or helix 18c having a substantially uniform inside diameter throughout its entire length. The upper portion of the helix defines a generally cylindrical outer peripheral surface whereas the lower portion thereof defines a substantially frustoconical outer peripheral surface. Thus, it will be apparent that the cross-sectional area of the lower portion of the helix 18c increases in the direction of its lower end.

A retaining member 22c projects from the upper end of the helix 18c and in a tangential direction opposite the direction of helical extent. The member 22c has a key 73 at its outer or free end, substantially as shown in FIG. 24. Unlike the previously described embodiments the helix 18c does not have a separate support member at its lower end. Rather the lower end or frustoconical portion of the helix performs the elevating and supporting function performed by the separate supporting member 24b disclosed in the previously described embodiment.

The insertion instrument 88 has a generally axially elongate body portion, indicated generally at 90 which has a radially disposed abutment surface 96 at its upper end. The upper part of the body portion 90 is generally cylindrical and the lower part is substantially frustoconical and diverging downwardly and terminating at a diametrically enlarged annular flange 92. A helical groove 94 formed in the body portion 90 threadably receives the correcting element 10c therein. The depth of the portion of the helical groove 94 defined by the cylindrical portion is substantially uniform. However the depth of the portion of the groove 94 defined the frustoconical portion increases in the direction of the flange 92. This arrangement permits the correcting element 10c to be threaded onto the body portion 90 so that the resulting assembly presents a substantially smooth uninterrupted peripheral surface.

A trocar, indicated generally at 98, is integrally connected to the body portion 90 and projects coaxially upwardly therefrom terminating in an upwardly diverging conical portion 100. An axially disposed locking slot 102 opens radially outwardly through the trocar 98 for receiving the locking key 73 therein.

The inserting instrument 88 further includes a coaxially extending shank 104 which projects downwardly from the annular flange 92 and which terminates at a diametrically enlarged handle 106 located at the lower or free end of the shank 104. A releasing rod 108 is disposed within an elongate passageway in the shank 104 and which extends through the flange 92 and opens into the locking slot 102. A handle or trigger 110 connected to the lower end of the releasing rod 108 projects radially outwardly through a slot in the shank 104. Thus, the releasing rod 108 is arranged for limited movement relative to the shank.

Preparatory to using the aforedescribed device the helix 18c is threaded downwardly onto the body portion 90. The retaining member 22c, which is resiliently self-biased to its retaining or deployed position shown in FIG. 24, is wound around the trocar 98 generally adjacent the abutment surface 96 with the locking key 73 disposed within the locking slot 102. Due to the position of the retaining member 22c relative to the helix 18c when the retaining member is wound about the trocar and to its inserting position in which it appears in FIG. 29 the connecting member 22c urges the helix 18c in a clockwise direction as viewed from above and toward the flange 92, thereby maintaining the correcting element 10c in assembly with the inserting tool 88. The trigger 110 is in its full line position or inactive position of FIG. 25 so that the ejector pin 108 is disposed below the locking key 73. The device is preferably marketed in the aforedescribed assembled condition in a sterile package or container ready for use.

The trocar 100 is pushed upwardly through the vaginal wall proximate the urethrovesical junction and through the abdominal fascia. The annular flange 92 engages the vaginal wall elevating it and thereby allowing the entire body portion 90 to be pushed upwardly through the vaginal wall and to a position slightly above the lower surface of the wall. When the support member 22c is disposed in position above the abdominal fascia the trigger 110 is operated to raise the ejector rod thereby dislodging the locking key 73 from the locking slot 102 whereby the retaining member 22c is resiliently self-biased to its retaining position above the abdominal fascia.

When the retaining member 22c has been deployed the inserting tool 88 is threadably disengaged from the correcting element 10c leaving the correcting element in an implanted position. In the latter position the lower end portion of the correcting element 10c may be substantially flush with or slightly above the vaginal wall. When the healing process is complete the correcting element 10c will be substantially encapsulated within body tissue. The tissue tends to migrate between and substantially fill the spaces within the helix 18c and between its various convolutions thereby providing a strong bond of scar tissue around substantially the entire portion of the helix 10c below the abdominal fascia. Thus, the implanted correcting element 10c will retain an associated portion of the vaginal wall in elevated position relative to the abdominal fascia.

In FIGS. 30-36 there is shown yet another device for correcting stress urinary incontinence which embodies the present invention and includes a correcting element 10d. Like the correcting elements previously described, the correcting element 10d is preferably made from a mechanically and biochemically reliable resilient flexible alloplastic material. It has an axially elongate connecting member or stem portion indicated at 18d and terminating at its upper end at an upwardly diverging parti-conical end portion 114. Preferably, and as shown the end portion is slightly rounded at its apex or tip. A plurality of arms 116 integrally connected to the stem are arranged in alternate series along the stem axis and alternately project from to one and the opposite side of the stem. Each arm 116 has an aperture 117 through its free end which extends in axially parallel relation to the stem axis. The various arms are resiliently self-biased to deployed positions shown in FIGS. 31 and 32. Each arm also has an implanting position wherein it is coiled inwardly toward the stem 18d and in FIG. 35 a typical arm 116 shown in its implanting position wherein the free end of the arm is disposed adjacent the stem.

Figures 30, 31, 32, 33, 34, 35, 36, 37, 38:
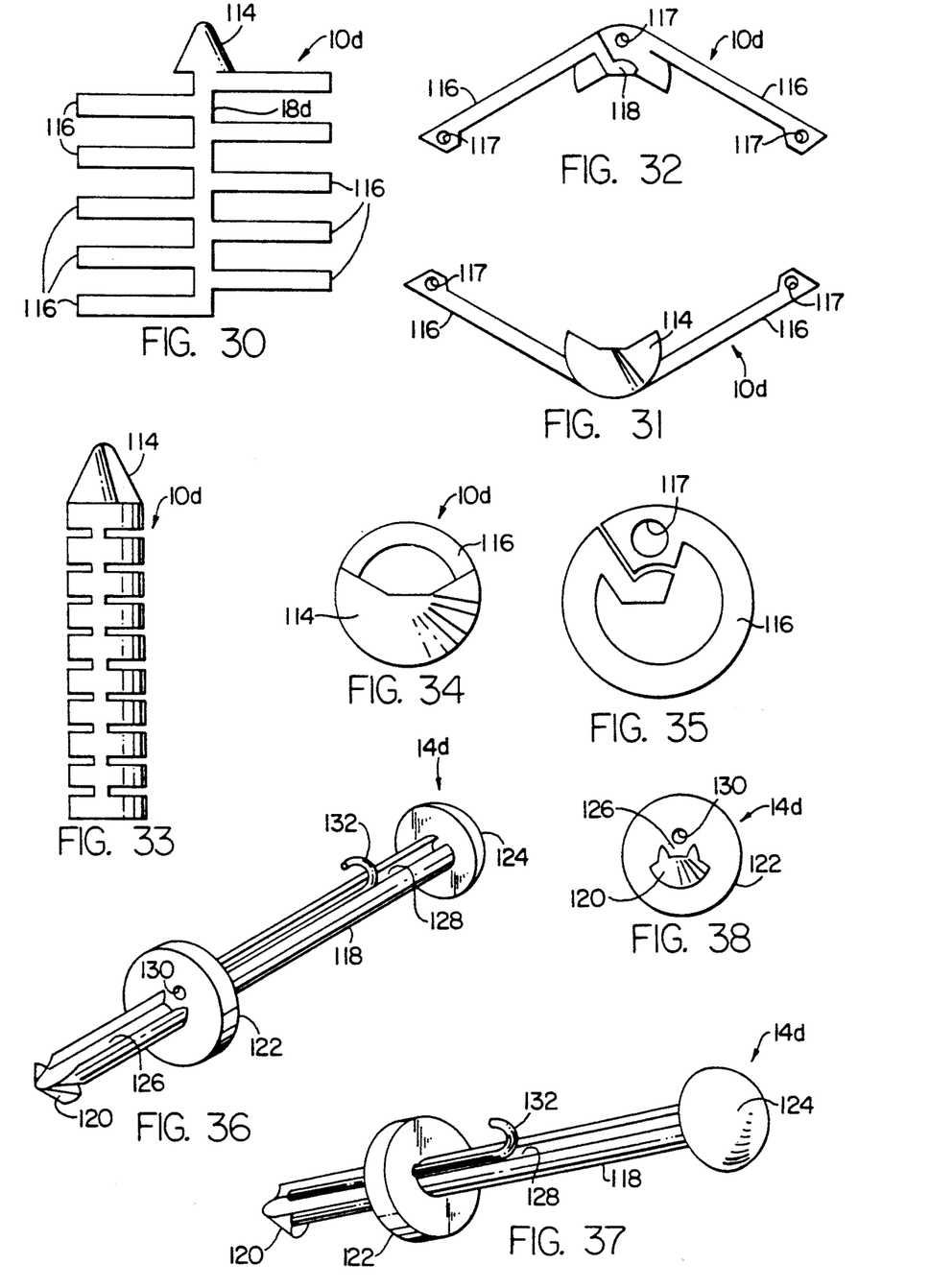
FIG. 30 is a side elevational view of a still another correcting element embodying the present invention.
FIG. 31 is a top plan view of the correcting element shown in FIG. 30.
FIG. 32 is a bottom plan view of the correcting element shown in FIG. 30.
FIG. 33 is a side elevational view of the correcting element of FIG. 30 shown in implanting position.
FIG. 34 is a somewhat enlarged top plan view of the correcting element as it appears in FIG. 33.
FIG. 35 is a somewhat enlarged top plan view of a typical arm shown in implanting position.
FIG. 36 is a perspective view of an instrument used for implanting the correcting device shown in FIGS. 30-35.
FIG. 37 is another perspective view of the instrument shown in FIG. 36.
FIG. 38 is a top plan view of the instrument shown in FIGS. 36 and 37.

The inserting tool for implanting the correcting element 10d is shown in FIGS. 36-38 and essentially comprises a trocar indicated generally at 14d. The trocar 14d has an axially elongate shank portion 118 which terminates at its upper end at a parti-conical tip 120 partially defined by sharp edges which extends to and are exposed at the tip, as best shown in FIG. 36. A diametrically enlarged radially disposed annular flange 122 is integrally connected to the shank 118 intermediate its ends, substantially as shown. A parti-spherical handle or knob 124 is attached to the lower end of the shank 118. The portion of the shank above the flange 122 defines a trough 126 which substantially complements an associated portion of the correcting element stem 18d. The cross-section of the parti-conical tip substantially complements the cross-sectional configuration of the correcting element end portion 114. An axially extending groove 128 is formed in the shank between the handle 124 and the flange 122 and communicates with an aperture 130. An axially elongate trigger pin or releasing rod 132 is disposed in the groove 128 and extends into the aperture 130, substantially as shown in FIGS. 36 and 37.

Preparatory to use the correcting element 10d is assembled with the inserting tool 14d. The correcting element 10d is positioned in the trough 126 with the inserting element tip 114 aligned with the inserting tool tip 120. The parti-conical inserting tool tip 120 cooperates with the parti-conical correcting element tip 114 to define a generally conical surface. The arms 116 are alternately wrapped in one and the opposite direction about the shank 118 and the free ends of the arms positioned within the trough 126. Thereafter, the trigger pin 132 is pushed within the groove 128 and through the aperture 130 and passes through the various apertures 117 in the free ends of the arms to lock the correcting element to the tool 14d with the various arms 116, 116 in the inserting position shown in FIG. 35.

The device hereinbefore described is preferably marketed in assembled condition, that is with the correcting element 10d assembled with the inserting tool 14d, and in a sterile package ready for use.

The correcting element 10d is implanted by forcibly pushing the tip of the tool 14d with the correcting element 10d thereon upwardly through the vaginal wall, through the space of Retaus, and through the abdominal fascia. The flange 122 is brought into engagement with associated portion of the vaginal wall and used to elevate the wall while one or more of the uppermost arms on the correcting element 10d are being moved to a position above the abdominal fascia. When the latter position has been attained the trigger pin 132 is withdrawn from the device allowing the various arms 116, 116 to be resiliently selfbiased to their respective deployed positions. Thereafter the inserting tool or trocar 14d is removed leaving the arms 116 deployed as aforedescribed. All of the arms 161 may be deployed above the vaginal wall. It will now be apparent that the uppermost arms 116 comprise retaining members which maintain the correcting element 10d in an elevating position above the abdominal fascia. The remaining arms 116 are embedded within tissue below the abdominal fascia and above the associated vaginal wall, cooperate with the latter tissue to retain the vaginal wall in elevated position, and comprise supporting members. As healing occurs tissue will migrate into the spaces between the various arms. The resulting scar tissue cooperates with the arms 116, 116 to maintain the vaginal wall in a substantially proper anatomical position whereby the incontinence condition is corrected.

I claim:

1. Device for correcting stress urinary incontinence comprising implant means for supporting an associated portion of the vaginal wall in elevated position relative to the abdominal fascia to correct stress urinary incontinence including an axially elongate connecting member having a first end portion, retaining means for securing said first end portion of the connecting member proximate the abdominal fascia to support said implant means and including at least one resilient flexible retaining member having a deployed position wherein it projects laterally outwardly from said connecting member and an inserting position wherein it is disposed laterally inwardly of said deployed position in the direction of said connecting member, said at least one retaining member being resiliently self-biased toward said deployed position, and supporting means attached to said connecting member in axially spaced relation to said at least one retaining means for supporting said portion of the vaginal wall in said elevated position.

2. Device for correcting stress urinary incontinence as set forth in claim 1 including a plurality of retaining members angularly spaced about the axis of said connecting member.

3. Device for correcting stress urinary incontinence as set forth in claim 2 wherein said connecting member comprises a stem and each of said retaining members is connected in cantilever position to said stem and generally disposed within a common radial plane of said stem in said deployed position.

4. Device for correcting stress urinary incontinence as set forth in claim 3 wherein said retaining members are equiangularly spaced about said axis.

5. Device for correcting stress urinary incontinence as set forth in claim 1 wherein said at least one retaining member is deflectable in one direction to said inserting position and including limiting means for preventing deflection of said at least one retaining member in a direction opposite said one direction.

6. Device for correcting stress urinary incontinence as set forth in claim 5 wherein said limiting means comprises an enlarged head on said first end portion of said connecting member.

7. Device for connecting stress urinary incontinence as set forth in claim 1 wherein said supporting means comprises a support member attached in cantilever position to said connecting member and extending generally radially outwardly therefrom.

8. Device for correcting stress urinary incontinence as set forth in claim 7 wherein said supporting means includes a generally U-shaped reverse bend portion integrally connected to said support member and having two legs disposed to opposite sides of said connecting member.

9. Device for correcting stress urinary incontinence as set forth in claim 1 wherein said supporting means comprises another end portion of said connecting member.

10. Device for correcting stress urinary incontinence as set forth in claim 9 wherein said connecting member comprises a helical member.

11. Device for correcting stress urinary incontinence as set forth in claim 10 wherein said other end portion is frustoconical.

12. Device for correcting stress urinary incontinence as set forth in claim 1 wherein said connecting member comprises a helical member.

13. Device for correcting stress urinary incontinence as set forth in claim 12 wherein said at least one retaining member in said deployed position extends tangentially from said first end portion of said helical member.

14. Device for correcting stress urinary incontinence as set forth in claim 13 wherein said connecting member comprises a helicoid.

15. Device for correcting stress urinary incontinence as set forth in claim 12 wherein said supporting means comprises an annular ring integrally connected to an end portion of said helical member and having a major dimension greater than the major radial dimension of said helical member.

16. Device for correcting stress urinary incontinence as set forth in claim 12 wherein at least a portion of said helical member has a frustoconical configuration.

17. Device for correcting stress urinary incontinence as set forth in claim 1 wherein said supporting means comprises at least one resilient flexible support member having a deployed position wherein it projects laterally outwardly from said connecting member and an inserting position wherein it is disposed laterally inwardly of said deployed position in the direction of said connecting member, said at least one support member being resiliently self-biased toward its deployed position.

18. Device for correcting stress urinary incontinence as set forth in claim 17 wherein said connecting member comprises a stem and the members comprising said at least one support member and said at least one retaining member are supported in cantilever position on said stem and arranged in alternate series along said stem and to one and an opposite side of an axial plane of said stem.

19. Device for correcting stress urinary incontinence as set forth in claim 18 wherein said at least one support member and said at least one retaining member comprise elongate arms and said arms are coiled about said connecting members in said inserting position.

20. Device for correcting stress urinary incontinence as set forth in claim 1 wherein said device includes instrument means for implanting said implant means and said implant means is carried by and separable from said instrument means.

21. Device for correcting stress urinary incontinence as set forth in claim 20 wherein said instrument means includes means for releasable securing said at least one retaining member in said inserting position.

22. Device for correcting stress urinary incontinence as set forth in claim 21 wherein said means for releasably securing said at least one retaining member comprises means for pinning said at least one retaining member to said instrument means.

23. Device for correcting stress urinary incontinence as set forth in claim 21 wherein said instrument means includes a cannula having an elongate cannula body defining a main channel and said cannula body comprises said means for releasably securing said at least one retaining member in said implanting position.

24. Device for correcting stress urinary incontinence as set forth in claim 23 wherein said instrument means includes positioning means for advancing said implant means relative to said cannula and to an implanting position.

25. Device for correcting stress urinary incontinence as set forth in claim 24 wherein said positioning means comprises a push rod.

26. Device for correcting stress urinary incontinence as set forth in claim 25 wherein said push rod comprises an integral part of said implant means.

27. Device for correcting stress urinary incontinence as set forth in claim 26 wherein said device includes signaling means for indicating the position of said implant means relative to said cannula as said implant means is advanced by said push rod.

28. Device for correcting stress urinary incontinence as set forth in claim 27 wherein said signaling means comprises a projection on said cannula extending into said channel and a series of detent recesses defined by said push rod for cooperating with said projection.

29. Device for correcting stress urinary incontinence as set forth in claim 23 including guiding means for manually manipulating said cannula.

30. Device for correcting stress urinary incontinence as set forth in claim 29 wherein said guiding means comprises an appendage on said cannula.

31. Device for correcting stress urinary incontinence as set forth in claim 20 wherein said instrument means includes piercing means for penetrating the vaginal wall.

32. Device for correcting stress urinary incontinence as set forth in claim 31 wherein said instrument means includes a cannula defining a main channel having an axis and said piercing means comprises a trocar received within said main channel.

33. Device for correcting stress urinary incontinence as set forth in claim 32 wherein said trocar complements and substantially fills an associated portion of said main channel.

34. Device for correcting stress urinary incontinence as set forth in claim 33 wherein said instrument means includes means for loading said implant means into said main channel including a cannula extension defining a secondary channel communicating with said main channel, said secondary channel having an axis.

35. Device for correcting stress urinary incontinence as set forth in claim 34 wherein said cannula extension comprises an integral branch of said cannula.

36. Device for correcting stress urinary incontinence as set forth in claim 34 wherein the axis of secondary channel is inclined relative to the axis of said main channel.

37. Device for correcting stress urinary incontinence as set forth in claim 34 wherein said secondary channel is coaxially aligned with said main channel and said cannula extension is separable from said cannula.

38. Device for correcting stress urinary incontinence as set forth in claim 20 wherein said implant means comprises a helical member threadably engaged with said instrument means.

* * * * *